(12) United States Patent
Lindh, Sr. et al.

(10) Patent No.: US 9,011,487 B2
(45) Date of Patent: Apr. 21, 2015

(54) BARBED SUTURES HAVING PLEDGET STOPPERS AND METHODS THEREFOR

(75) Inventors: David C. Lindh, Sr., Flemington, NJ (US); Jesse G. Nawrocki, Annandale, NJ (US); Dennis L. Furman, East Windsor, NJ (US); Krasimira Hristov, Belle Mead, NJ (US); Jason T. Perkins, Bethlehem, PA (US)

(73) Assignee: Ethicon, Inc., Somerville, NJ (US)

( * ) Notice: Subject to any disclaimer, the term of this patent is extended or adjusted under 35 U.S.C. 154(b) by 390 days.

(21) Appl. No.: 12/549,046

(22) Filed: Aug. 27, 2009

(65) Prior Publication Data

US 2011/0054522 A1 Mar. 3, 2011

(51) Int. Cl.
*A61B 17/04* (2006.01)
*A61B 17/06* (2006.01)
*A61B 17/00* (2006.01)

(52) U.S. Cl.
CPC ........ *A61B 17/06166* (2013.01); *A61B 17/0401* (2013.01); *A61B 2017/00243* (2013.01); *A61B 2017/0404* (2013.01); *A61B 2017/0406* (2013.01); *A61B 2017/0461* (2013.01); *A61B 2017/06057* (2013.01); *A61B 2017/06176* (2013.01)

(58) Field of Classification Search
CPC ..................... A61B 17/0401; A61B 17/06166; A61B 2017/0406; A61B 2017/06176; A61B 2017/06057; A61B 2017/06185; A61B 17/06; A61B 2017/0404
USPC ......... 606/228–232, 139, 144, 148, 219, 220; 600/30, 37; 227/175.1–182.1; 623/2.38, 2.41
See application file for complete search history.

(56) References Cited

U.S. PATENT DOCUMENTS

| 3,608,095 | A | * | 9/1971 | Barry | 128/898 |
| 4,510,934 | A | * | 4/1985 | Batra | 606/231 |
| 4,546,769 | A |   | 10/1985 | Planck et al. | |
| 4,549,545 | A | * | 10/1985 | Levy | 606/228 |
| 4,823,794 | A | * | 4/1989 | Pierce | 606/232 |

(Continued)

FOREIGN PATENT DOCUMENTS

WO WO 2009097556 A2 8/2009
WO WO 2009129251 A2 10/2009

OTHER PUBLICATIONS

Ethibond Excel Polyester Suture, http://ecatalog.ethicon.com/sutures-non-absorbable/view/ethibond-excel-suture, 14 pp. (2009).

(Continued)

*Primary Examiner* — Gregory Anderson
*Assistant Examiner* — Christopher L Templeton
(74) *Attorney, Agent, or Firm* — Doherty IP Law Group LLC

(57) ABSTRACT

A surgical suture includes an elongated core having a first leg and a second leg, a first set of barbs projecting from the first leg of the core, and a second set of barbs projecting from the second leg of the core. The suture has a stop projecting from the core that is located between the first and second sets of barbs, and a braid surrounding the elongated core and the stop for strengthening the suture. The suture includes a pledget having first and second openings extending through the pledget, with the first leg extending through the first pledget opening, the second leg extending through the second pledget opening, and the stop extending between the first and second pledget openings.

18 Claims, 9 Drawing Sheets

(56) References Cited

U.S. PATENT DOCUMENTS

| | | | |
|---|---|---|---|
| 5,217,495 A * | 6/1993 | Kaplan et al. | 623/13.18 |
| 5,219,359 A * | 6/1993 | McQuilkin et al. | 606/232 |
| 5,366,480 A * | 11/1994 | Corriveau et al. | 606/233 |
| 5,383,904 A * | 1/1995 | Totakura et al. | 606/228 |
| 5,593,424 A * | 1/1997 | Northrup, III | 606/232 |
| 5,645,568 A | 7/1997 | Chervitz et al. | |
| 5,654,568 A * | 8/1997 | Nakao | 257/324 |
| 5,733,308 A * | 3/1998 | Daugherty et al. | 606/232 |
| 5,895,419 A * | 4/1999 | Tweden et al. | 623/2.36 |
| 5,931,855 A | 8/1999 | Buncke et al. | |
| 6,029,806 A * | 2/2000 | Cerwin et al. | 206/63.3 |
| 6,066,160 A * | 5/2000 | Colvin et al. | 606/232 |
| 6,280,474 B1 * | 8/2001 | Cassidy et al. | 623/16.11 |
| 6,475,229 B1 | 11/2002 | Pagedas | |
| 6,506,197 B1 * | 1/2003 | Rollero et al. | 606/148 |
| 6,610,071 B1 * | 8/2003 | Cohn et al. | 606/148 |
| 6,776,789 B2 * | 8/2004 | Bryant et al. | 606/213 |
| 7,744,611 B2 * | 6/2010 | Nguyen et al. | 606/151 |
| 2003/0088270 A1 * | 5/2003 | Lubbers et al. | 606/213 |
| 2003/0149447 A1 * | 8/2003 | Morency et al. | 606/228 |
| 2003/0236555 A1 * | 12/2003 | Thornes | 606/232 |
| 2004/0106847 A1 * | 6/2004 | Benderev | 600/37 |
| 2004/0116963 A1 * | 6/2004 | Lattouf | 606/224 |
| 2004/0147958 A1 * | 7/2004 | Lam et al. | 606/232 |
| 2004/0167573 A1 | 8/2004 | Williamson et al. | |
| 2005/0192630 A1 * | 9/2005 | Maas et al. | 606/224 |
| 2005/0240224 A1 * | 10/2005 | Wu | 606/228 |
| 2005/0267532 A1 | 12/2005 | Wu | |
| 2005/0283192 A1 * | 12/2005 | Torrie et al. | 606/228 |
| 2006/0229675 A1 * | 10/2006 | Novoa et al. | 606/232 |
| 2007/0005110 A1 | 1/2007 | Collier et al. | |
| 2007/0038249 A1 * | 2/2007 | Kolster | 606/228 |
| 2007/0224237 A1 | 9/2007 | Hwang et al. | |
| 2007/0257395 A1 | 11/2007 | Lindh et al. | |
| 2008/0046009 A1 * | 2/2008 | Albertorio et al. | 606/232 |
| 2008/0177302 A1 * | 7/2008 | Shurnas | 606/228 |
| 2008/0195148 A1 * | 8/2008 | Cook et al. | 606/232 |
| 2008/0255611 A1 | 10/2008 | Hunter | |
| 2008/0281357 A1 * | 11/2008 | Sung et al. | 606/232 |
| 2009/0099597 A1 * | 4/2009 | Isse | 606/228 |
| 2009/0171143 A1 | 7/2009 | Chu et al. | |
| 2009/0248071 A1 * | 10/2009 | Saint et al. | 606/232 |
| 2009/0306710 A1 | 12/2009 | Lindh | |
| 2009/0312791 A1 | 12/2009 | Lindh | |
| 2010/0023055 A1 | 1/2010 | Rousseau | |
| 2010/0160961 A1 | 6/2010 | Nawrocki | |

OTHER PUBLICATIONS

Written Opinion of the International Searching Authority for International Application No. PCT/US2010/046435 dated Feb. 28, 2012, 8 pp.

* cited by examiner

BARBED SUTURES HAVING PLEDGET STOPPERS AND METHODS THEREFOR

CROSS REFERENCE TO RELATED APPLICATIONS

The present application is related to commonly assigned U.S. patent application Ser. No. 12/548,984, entitled "Automated Systems and Methods for Making Braided Barbed Sutures," filed on even date herewith, the disclosure of which is hereby incorporated by reference herein.

BACKGROUND OF THE INVENTION

1. Field of the Invention

The present invention generally relates to surgical sutures, and more specifically relates to sutures used for affixing prosthetic devices to tissue.

2. Description of the Related Art

Surgical sutures are used to close wounds and surgical incisions, and to repair damaged or severed muscles, vessels, and tissue. Typically, the suture is attached at one end to a needle, and the needle is drawn through tissue to form one or more loops holding the tissue together. The suture is subsequently tied off in one or more knots so that the tissue will remain drawn together.

Although sutures are very effective for closing wounds, there are a number of issues associated with using conventional sutures. Many of these issues are directly related to using knots to secure the sutures in place. If the knots are not tied properly, defects may arise including slippage, knot breakage, and re-opening of the wound.

In response to the obstacles associated with conventional sutures, barbed sutures have been developed. Unlike conventional sutures, barbed sutures have projecting barbs that allow the suture to be used to close wounds, approximate tissue, tighten tissue, and attach prosthetic devices—all without using knots. Fixing conventional sutures with knots requires the knots to be pushed down toward the tissue to assure proper tensioning and fixation of the sutures. In contrast, barbed sutures achieve proper tensioning and fixation by applying tension to the suture. For example, U.S. Pat. No. 5,931,855 discloses barbed sutures that are used for cosmetic procedures such as brow-lifts and face-lifts.

In some procedures, it is desirable to use barbed sutures to secure prosthetic devices such as bioprosthetic heart valves. For example, in certain embodiments of commonly assigned U.S. Patent Application Publication No. 2007/0005110, the disclosure of which is hereby incorporated by reference herein, braided barbed sutures are disposed in a heart valve sewing ring by first passing the sutures through an annulus and then passing the sutures through the valve sewing ring. First and second ends of the barbed suture may be passed through the openings of a pledget for securely seating the suture against the valve sewing ring. The pledget is typically positioned in a central region of the barbed suture, which is located between opposing sets of barbs. Approximately 12-20 sets of braided barbed sutures are used around the perimeter of the valve for securing the valve in place. The valve sewing ring is then parachuted down the sets of barbed sutures and seated in place within the annulus. After the sewing ring has been parachuted in a downward direction, the barbs prevent the sewing ring from being moved in the opposite, upward direction. The barbs hold the sewing ring in place without using knots.

In spite of the above advances, there remains a need for sutures, suture systems and suturing methods that more securely and reliably hold the sutures in place and minimize slippage of the sutures and/or the pledgets used in combination with the sutures. In addition, there remains a need for suture systems that simplify surgical procedures and minimize the likelihood of surgical error. There also remains a need for sutures that are able to more easily pass through tissue and sewing rings without causing damage.

SUMMARY OF THE INVENTION

In one embodiment, a surgical suture includes an elongated core having a first leg and a second leg, and a stop projecting from the elongated core between the first and second legs. The suture may include a first set of barbs projecting from the first leg, and a second set of barbs projecting from the second leg, whereby the stop projects from a central region of the elongated core, which is preferably located between the first and second sets of barbs. In one embodiment, the first set of barbs project in a first direction and the second set of barbs project in a second direction that is opposite the first direction. In one embodiment, the barbs of the first and second sets of barbs are desirably flexible, and the stop is preferably less flexible than the barbs of the first and second sets of barbs.

In one embodiment, the barbed suture may be braided such as by winding a plurality of filaments wound around the elongated core and the stop. The wound filaments desirably form a braid extending along the length of the elongated core that adds strength to the suture, particularly for instances where the suture is under tension. In one embodiment, the barbs preferably project through the interstices of the braid.

In one embodiment, the stop is integrally formed with the core. The stop is preferably fixed in place between the opposing sets of barbs. The stop preferably defines the largest cross-sectional dimension of the core. In one embodiment, the stop includes at least one saddle projecting from the core. The at least one saddle may have a longitudinal axis that extends along the longitudinal axis of the core. The at least one saddle may have a concave lateral surface. In one embodiment, the terminology "concave lateral surface" describes a surface that extends along the length of the core. In one embodiment, the stop has two saddles including a first saddle projecting from a first side of the core and a second saddle projecting from a second side of the core. The first and second saddles of the stop may be coplanar.

In one embodiment, the suture includes a pledget having first and second openings extending therethrough. The barbed suture may be assembled with the pledget by passing the first leg through the first pledget opening and the second leg through the second pledget opening. After the first and second legs have been passed through the pledget openings, the stop preferably extends between the first and second pledget openings. In one embodiment, the stop has a length that generally matches the spacing between the first and second openings of the pledget. In one embodiment, the spacing between the first and second pledget openings is measured from the inner edge of one opening to the inner edge of the other opening. In one embodiment, when the barbed suture is assembled with the pledget, the pledget is positioned between the first and second barbed legs, and a major face of the stop opposes a major face of the pledget.

In one embodiment, a surgical suture includes an elongated core including a first leg, a second leg, and a central region located between the first and second legs. The suture preferably includes a first set of barbs projecting from the first leg of the core, a second set of barbs projecting from the second leg of the core, and a stop projecting from the central region of the core.

The suture may include a braid formed around the elongated core and the stop for strengthening the suture, particularly for instances where the suture is under tension. The suture may include a pledget having first and second openings extending therethrough, whereby the first leg desirably extends through the first pledget opening, the second leg desirably extends through the second pledget opening, and the stop extends between the first and second pledget openings.

In one embodiment, a surgical suture preferably includes an elongated core having a first leg and a second leg, a first set of barbs projecting from the first leg, a second set of barbs projecting from the second leg, a stop projecting from the core and being located between the first and second sets of barbs, and a braid surrounding the elongated core and the stop for strengthening the suture. The braid desirably includes a plurality of filaments wound around the elongated core and the stop, whereby the barbs of the first and second sets of barbs extend through the interstices of the braid.

In one embodiment, the suture may be used in conjunction with a pledget having first and second openings extending therethrough, whereby the first leg of the suture extends through the first pledget opening, the second leg extends through the second pledget opening, and the stop extends between the first and second pledget openings.

In one embodiment, the stop may include a double saddle stop extending from the core of a suture. In one embodiment, the stop may include a single saddle stop projecting from the core of a suture. In yet another embodiment, the stop preferably includes a tab projecting from the core of a suture. The stop is preferably affixed to the core and is adapted to remain stationary relative to the core. The stop may be utilized with barbed and unbarbed sutures, and braided or unbraided sutures.

In one embodiment, a barbed suture may have a plurality of barbs including a leading barb that has a more gradual outward slope than the trailing barbs. The leading barb may have an arrowhead shape that provides for a smoother transition from the core of the suture to the full-sized barbs that trail the leading barb. The leading arrowhead shaped barb may have a longitudinal length that is greater than the longitudinal length of one or more of the trailing barbs. In one embodiment, the leading barb has a length that is about 3-4 times greater than the length of the trailing barbs. As used above, the "term" length means a length measured along the longitudinal axis of the suture. In one embodiment, a barbed suture having an arrowhead shaped leading barb may include an unbraided barbed insert. In one embodiment, a barbed suture having an arrowhead shaped leading barb may be a braided barbed suture including a barbed insert and filaments wound around the barbed insert to form a braid. As such, the term "core" may be used to describe the elongated core of a barbed insert, or the elongated non-barbed filament positioned along the longitudinal axis of a barbed insert.

These and other preferred embodiments of the present invention will be described in more detail below.

DETAILED DESCRIPTION

Figure 1A:
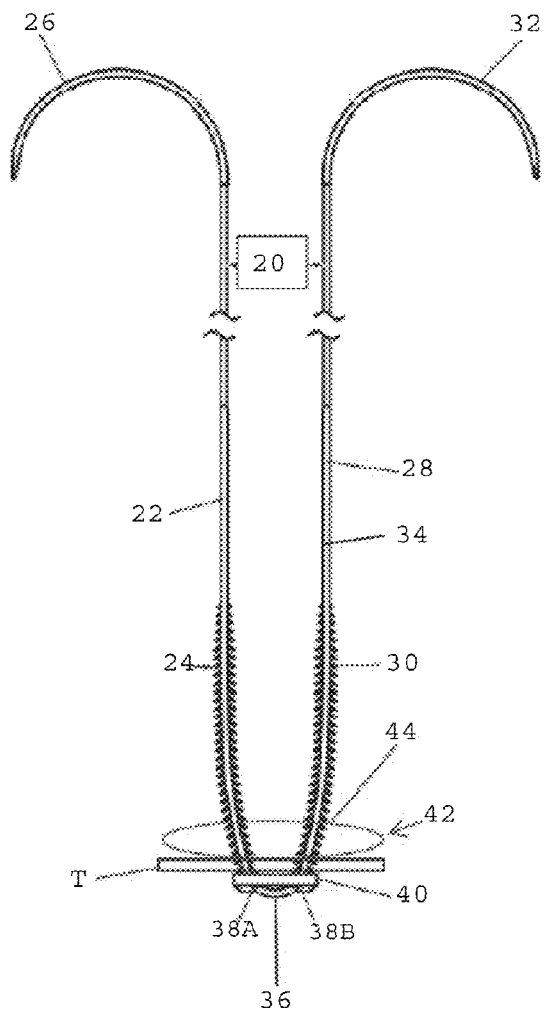
FIG. 1A shows a front elevational view of a barbed suture including a pledget.
Figure 1B:
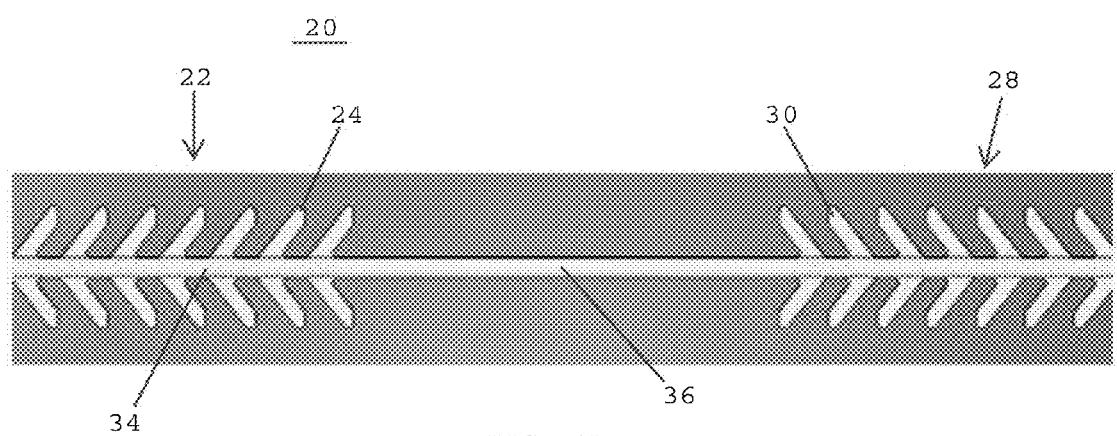
FIG. 1B shows a central region of the barbed suture shown in FIG. 1A.

Referring to FIGS. 1A and 1B, a bidirectional barbed suture 20 includes a first leg 22 having a first set of barbs 24 and a first suture needle 26 provided at the distal end of the first leg. The bidirectional barbed suture 20 includes a second leg 28 having a second set of barbs 30 and a second suture needle 32 provided at the distal end of the second leg. The first set of barbs 24 extend in an opposite direction from the second set of barbs 30. The barbed suture 20 includes a core 34, and the first and second sets of barbs 24, 30 project outwardly from the core 34. The core 34 has a central region 36 that is located and extends between the first and second sets of barbs 24, 30. Before or during a surgical procedure, the first and second legs 22, 28 of the bidirectional barbed suture 20 are passed through respective first and second openings 38A, 38B of a pledget 40. In one embodiment, the first suture needle 26 is passed through the first opening 38A of the pledget 40 and the second suture needle 32 is passed through the second opening 38B of the pledget 40. The first and second legs 22, 28 are pulled through the pledget openings so that the pledget 40 is positioned within the central region 36 of the core 34, which is between the first set of barbs 24 and the second set of barbs 30.

Referring to FIG. 1A, the bidirectional barbed suture 20 may be used to secure a valve sewing ring 42 to tissue T. The valve sewing ring 42 is positioned adjacent the tissue T and the first suture needle 26 is pulled through the tissue T and the valve sewing ring 42 so that at least some of the first barbs 24 on the first leg 22 extend from the top surface 44 of the valve sewing ring 42. The second suture needle 32 is pulled through the tissue T and the valve sewing ring 42 so that at least some of the second barbs 30 on the second leg 28 extend from the top surface 44 of the valve sewing ring 42.

Figure 2A:
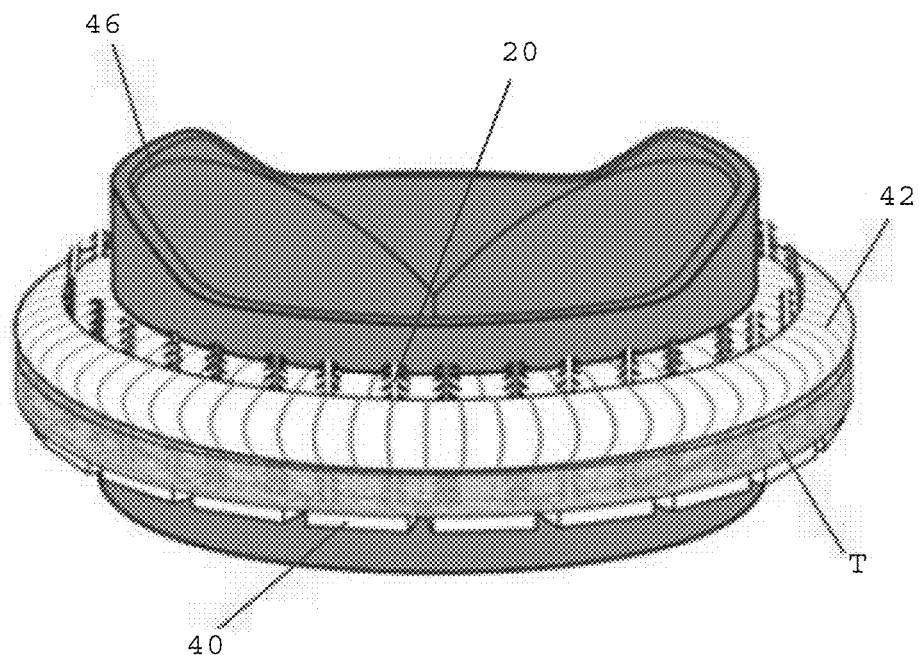
FIGS. 2A-2B show a plurality of barbed sutures used for securing a prosthetic device to tissue.
Figure 2B:
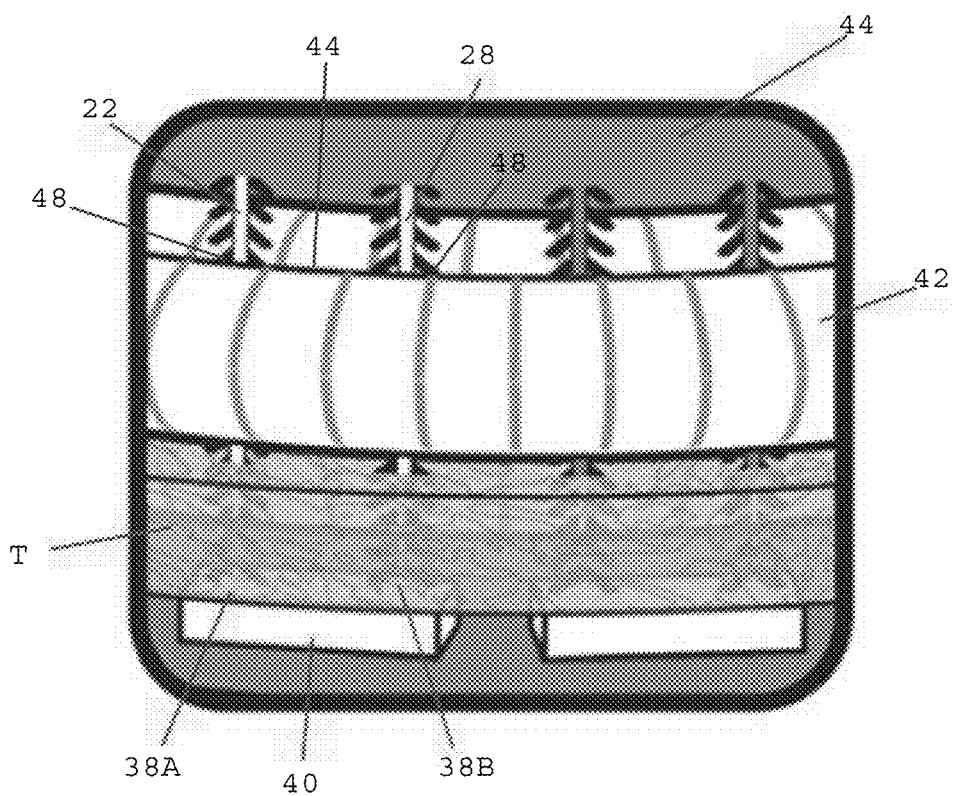

Referring to FIG. 2A, a plurality of bidirectional barbed sutures and pledgets are used around the perimeter of the valve sewing ring 42 for securing a prosthetic device 46, such as a heart valve, to the tissue T. As shown in FIG. 2A, the pledget 40 is preferably aligned with the central region 36 (FIG. 1B) of the core of the barbed suture 20. Referring to FIG. 2B, the first and second legs 22, 28 of each bidirectional barbed suture extend along axes that are substantially parallel with one another. The spacing between the first and second legs 22, 28 of the suture is controlled by the spacing between the openings 38A, 38B in the pledget 40. Some of the barbs 40 on the legs 22, 28 engage the top surface 44 of the sewing ring 42 for securing the sewing ring to the tissue T.

Figure 3A:
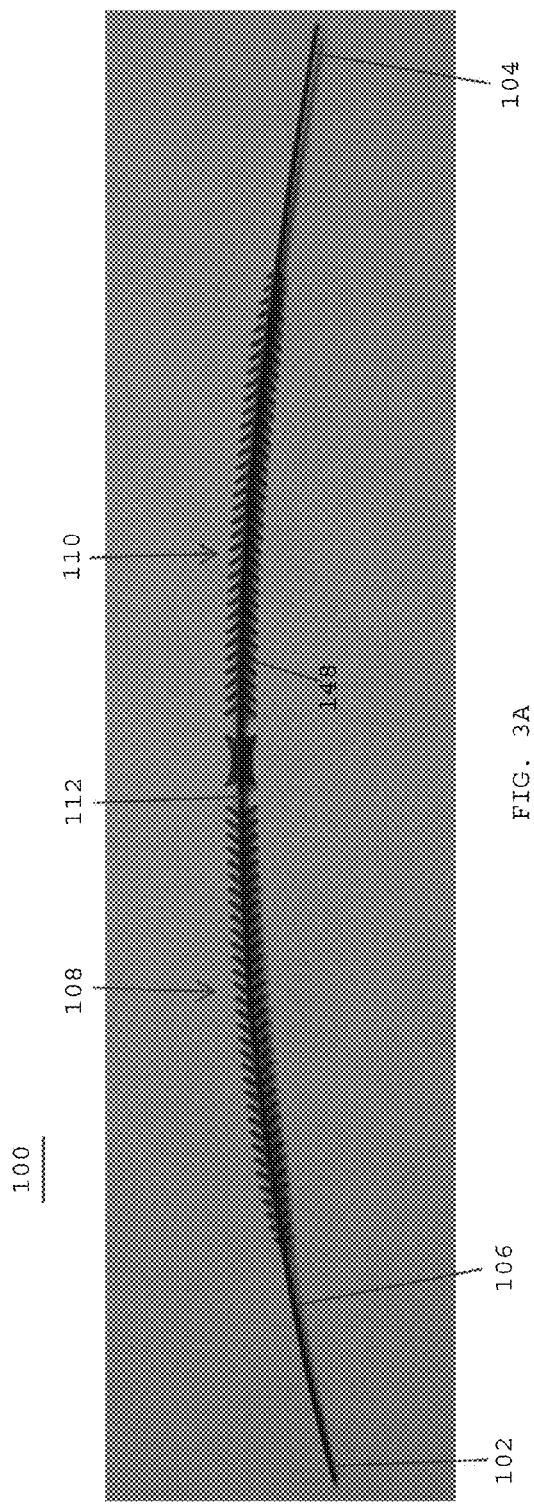
FIGS. 3A and 3B show a barbed suture having a stopper in a central region thereof, in accordance with one embodiment of the present invention.

Referring to FIG. 3A, in one embodiment, a bidirectional barbed suture 100 has a first end 102 and a second end 104. The first and second ends 102, 104 of the barbed suture may be connected to respective hooks, needles or tissue piercing elements for passing the respective first and second ends 102, 104 through pledget openings, tissue and/or prosthetic devices. The bidirectional barbed suture 100 preferably includes an elongated core 106 that extends between the first and second ends 102, 104, and a plurality of barbs 148 projecting outwardly from the core 106.

In one embodiment, the bidirectional barbed suture 100 includes a first set of barbs 108 projecting from the core 106 and an opposing second set of barbs 110 projecting from the core 106. The first and second sets of barbs 108, 110 desirably project in opposite directions. The core 106 of the bidirectional barbed suture 100 preferably includes a central region 112 that extends between the opposing first and second sets of barbs 108, 110.

Figure 3B:
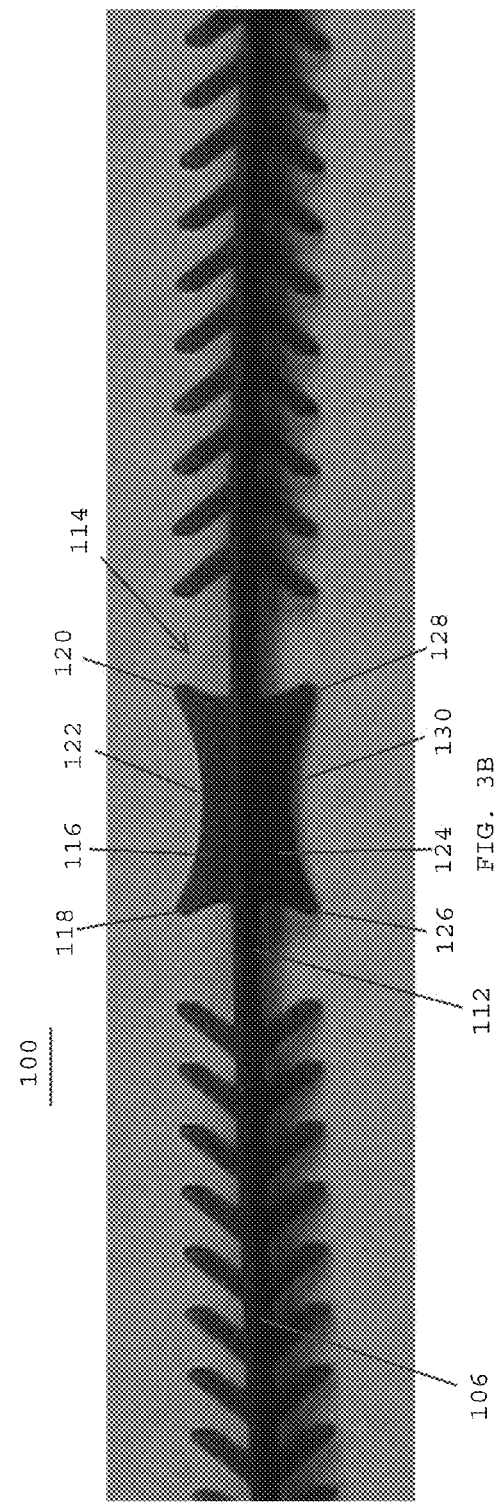

Referring to FIGS. 3A and 3B, in one embodiment, the bidirectional barbed suture includes a stop 114 located within the central region 112 of the core 106. The stop preferably projects outwardly from the core. In one embodiment, the stop 114 is desirably integrally formed with the core. In one embodiment, the stop 114 preferably includes a first saddle 116 having a first end 118 and a second end 120, and a concave top surface 122 that extends between the first and second ends 118, 120. The stop 114 preferably includes a second saddle 124 having a first end 126 and a second end 128, and a concave surface 130 extending between the first end 126. In one embodiment, the first and second saddles 116, 124 project from opposite sides of the core and are coplanar. The first and second saddles 116, 124 may be integrally formed with the core.

In one embodiment, the stop 114 is preferably incorporated into the bidirectional barbed suture 100 within a central region of the suture 100 so as to limit the mobility of a pledget and/or to improve the performance of the suture. Although the present invention is not limited by any particular theory of operation, it is believed that providing a bidirectional barbed suture with a stop located between first and second sets of opposing barbs improves the holding strength of the barbed suture and prevents unwanted movement of the pledget after the sutures have been tightened. If, during a surgical procedure, one leg of a conventional barbed suture is over-tightened while securing a prosthetic device, the possibility exists to pull the barbs on the opposing second leg through a pledget hole causing the barbed suture to back out of the pledget and potentially fail. The present invention seeks to minimize these risks by providing a barbed suture having a stop located between the opposing first and second barbed sections. The centrally located stop cooperates with the pledget to form an improved tissue buttress that essentially decouples each leg of the suture from one another, which allows for each leg of the suture to be seated independently of one another for reducing the potential for device failure. In one embodiment, the stop may be used as a tissue buttress by itself without requiring a pledget, thereby eliminating the need to use a pledget with the barbed suture. Embodiments using the stop as a stand-alone tissue buttress may also eliminate the potential for the suture to back-out because the stop is preferably a fixed part of the suture.

The barbed sutures having a stop disclosed in the present application may be used in a wide variety of surgical procedures where fixation is necessary. In one embodiment, the present invention may be used for heart valve fixation procedures. The present invention may also be used for other medical applications such as hernia repair, anastomoses, wound closure, organ support (e.g., pexy procedures e.g., with pelvic organ support or tongue support for the treatment of obstructive sleep apnea), trauma repair (where rapid tissue repair is needed), cosmetic procedures, and other surgical procedures requiring a distribution of forces along the surface of tissue to minimize direct suture pressure on tissue. The barbed sutures disclosed herein may also be used for wound closure. In one embodiment, an incision may be closed using a barbed suture. In one embodiment, a surgical method includes passing a suture through both sides of the beginning end of an incision, tying a knot at the beginning end of the incision, and then running a stitch to the opposite end of the incision, then running a stitch to the opposite end of the incision and placing a stitch in the opposite direction. Another technique involves starting the suture a short distance from the beginning end of the incision, suturing back to the beginning of the incision, and then performing a running stitch to the opposite end of the incision, then running a stitch to the opposite end of the incision and placing a stitch in the opposite direction.

Figure 4:
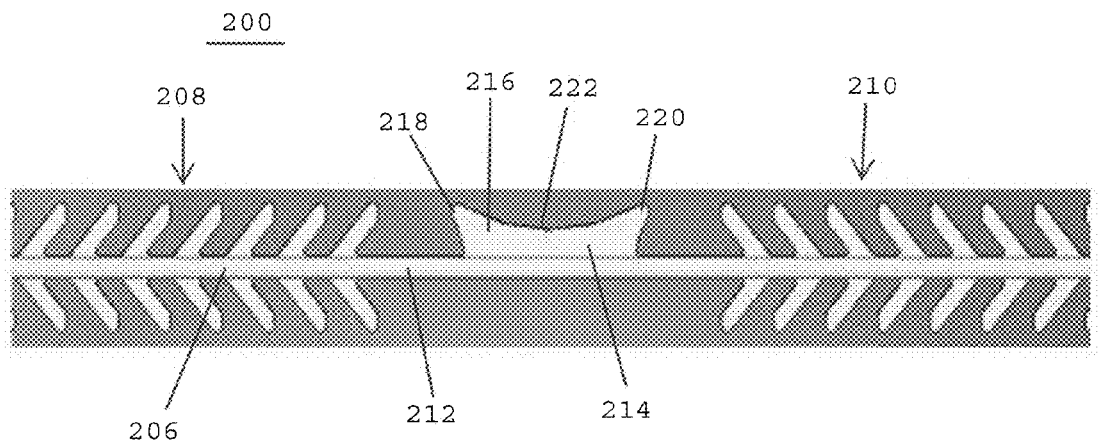
FIG. 4 shows a barbed suture having a stopper in a central region thereof, in accordance with another embodiment of the present invention.

Referring to FIG. 4, in one embodiment, a bidirectional barbed suture 200 includes an elongated core 206, a first set of barbs 208, and a second set of barbs 210 that project in an opposite direction from the first set of barbs 208. The elongated core 206 includes a central region 212 that extends between the first and second sets of barbs 208, 210. The suture 200 preferably includes a stop 214 projecting from the central core region. The stop 214 preferably includes a single saddle 216 having a first end 218, a second end 220, and a concave surface 222 extending between the first and second ends 218, 220. The stop 214 is preferably permanently affixed to and/or integrally formed with the core 206 for remaining within the central region 212 of the barbed suture 200.

Figure 5:
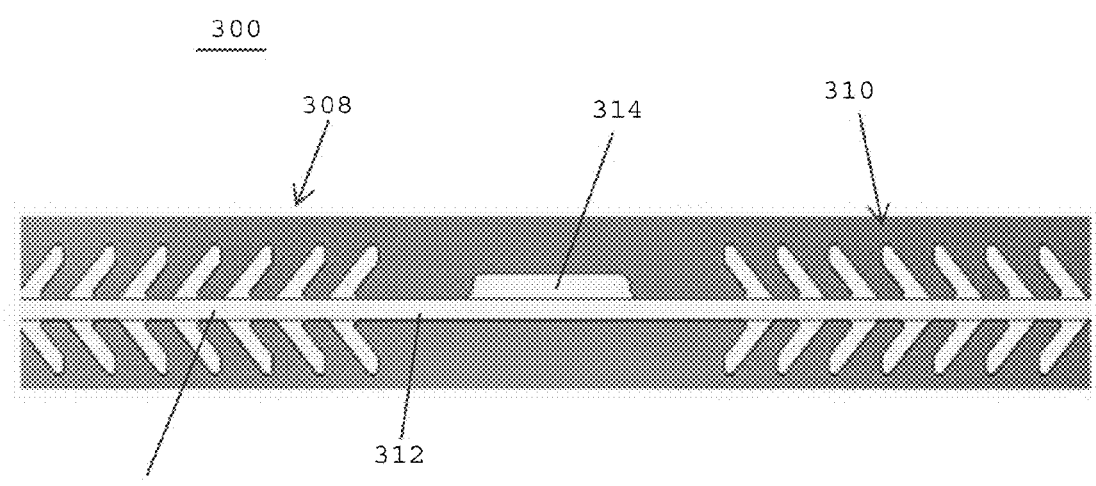
FIG. 5 shows a barbed suture having a stopper in a central region thereof, in accordance with yet another embodiment of the present invention.

Referring to FIG. 5, in one embodiment, a bidirectional barbed suture 300 includes a core 306, a first set of barbs 308, and an opposing second set of barbs 310. The opposing first and second sets of barbs preferably extend in opposite directions. The core 306 desirably includes a central region 312 extending between the first and second sets of barbs 308, 310. The central region 312 of the core 306 preferably includes a tab-shaped stop 314 projecting from the central core region 312. The tab-shaped stop 314 is preferably positioned between the first set of barbs 308 and a second set of barbs 310.

In one embodiment, providing a pledget stop on a barbed suture enables a pledget to function as a more effective tissue buttress. Bench top testing was performed in order to quantify the average maximum load necessary to pull a barbed device having a pledget stopper through a pledget hole when securing an individual leg of the suture during surgery. An Instron testing device with a 20 lb capacity load cell was utilized for testing at a crosshead speed of 5 in/min. The needle from one end of the barbed suture was manually passed through a hole in a sheet of pledget material to a point where the barbed insert section was just below the plane of the pledget material.

The end of the suture that had been passed through the pledget hole was secured in the upper Instron grip and the cross-head motion was initiated for pull through. The end of test criteria for pull through was approximately the point at which the entire barbed insert section had passed through the pledget hole. Therefore, the first section of barbs collapsed in the preferred direction as it passed through the pledget hole while the opposing set of barbs was bent back on itself. Different pledget stopper designs were incorporated between these opposing barbed sections for evaluation. A design that requires greater force to pull the pledget stopper through the pledget hole will be more effective at protecting against the over-tightening of the device that could take place while seating the heart valve during surgery.

The table below summarizes the average maximum loads recorded at the stop for the respective pledget stopper embodiments shown in FIGS. 3A, 4, and 5. In one preferred embodiment, the pledget comprises a biocompatible material such as Polytetrafluoroethylene (PTFE) pledget material, also known as TEFLON®, however, other biocompatible materials may also be used. Ten devices were tested for each of the pledget stopper designs shown herein. They were compared to a control suture, namely a barbed suture which has no pledget stopper.

TABLE I

Average maximum load (lbf) for each pledget stopper design.

| Design | Teflon ® Pledget Material |
|---|---|
| Tab Shaped Stop-FIG. 5 | 0.03 ± 0.01 |
| Single Saddle Stop-FIG. 4 | 1.0 ± 0.2 |
| Two Saddle Stop-FIG. 3A | 3.7 ± 0.5 |

Figure 6:
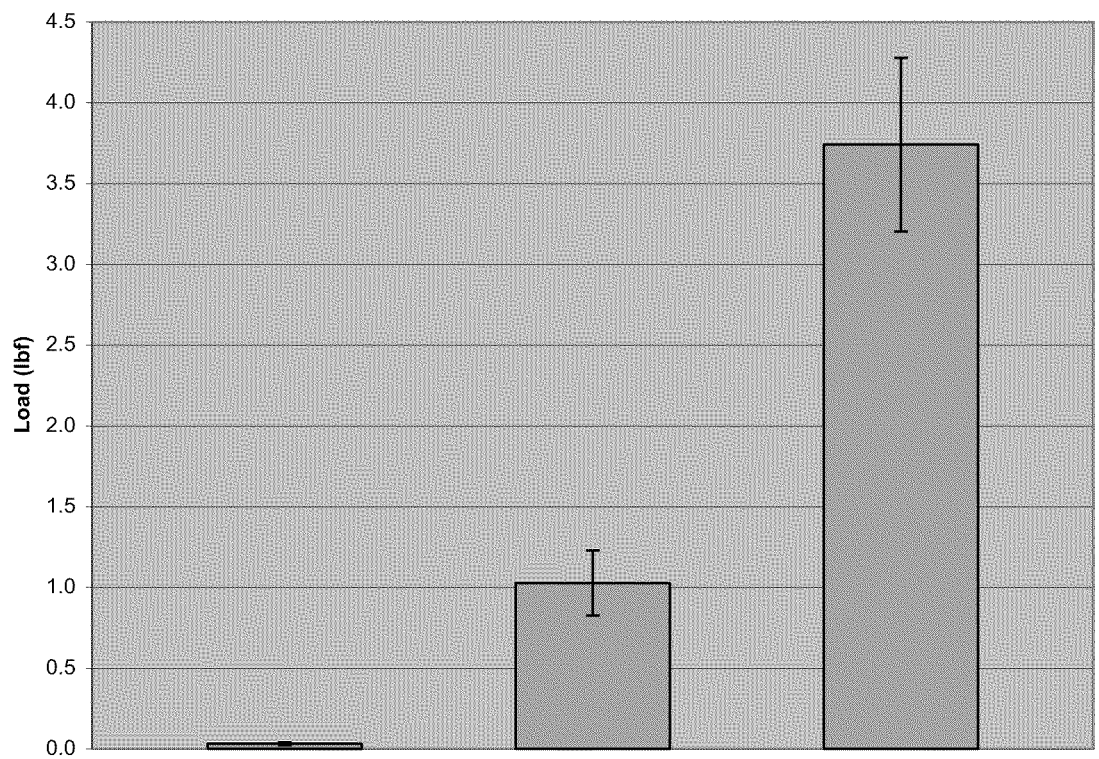
FIG. 6 is a chart showing the results of load testing on the barbed sutures shown in FIGS. 3B, 4, and 5 respectively.

FIG. 6 represents the above data in a plotted format. From the FIG. 6 data, it is evident that the two saddle stop embodiment of FIG. 3A required the greatest load to pull the stop through a pledget hole. The single saddle stop embodiment of FIG. 4 required the second greatest load, and the tab-shaped stop embodiment shown in FIG. 5 required less load than the embodiments of FIGS. 3A and 4. However, all three of the stop embodiments shown in FIGS. 3A, 4, and 5 provided significantly improved results over a bidirectional barbed suture that does not have a stop located between opposing sets of barbs.

In one embodiment, the bidirectional barbed sutures shown in FIGS. 3A-3B, 4, and 5 may be braided as disclosed in one or more embodiments of commonly assigned U.S. patent application Ser. No. 12/548,984, entitled "Automated Systems and Methods for Making Braided Barbed Sutures," filed on even date herewith, the disclosure of which is hereby incorporated by reference herein.

Figure 7A:
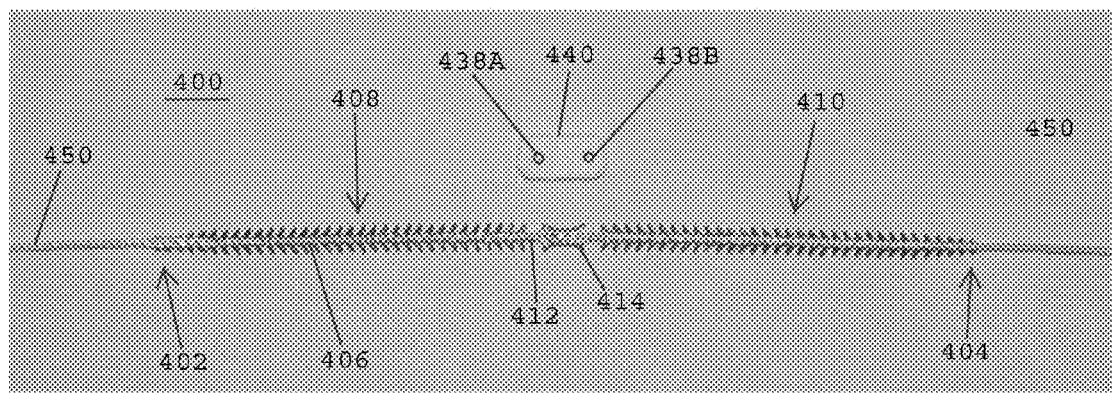
FIG. 7A shows a braided barbed suture having a stopper that is used in conjunction with a pledget, in accordance with one embodiment of the present invention.

Referring to FIG. 7A, in one embodiment, a bidirectional barbed suture 400 such as that shown in FIGS. 3A and 3B is passed through a braiding system for winding filaments around the core of the suture to form a braid 450. The braided barbed suture 400 includes a first end 402, a second end 404 and an elongated core 406 that extends between the first and second ends. The braided barbed suture 400 preferably includes a first set of barbs 408 and a second set of barbs 410 that extend in an opposite direction from the first set of barbs 408. The first and second sets of barbs preferably project outwardly from the core 406. The elongated core 406 includes a central region 412 and a stop 414 projecting outwardly from the core 406 within the central region 412. The braided barbed suture 400 preferably includes a plurality of filaments wound around the elongated core 406 and the stop 414. The braid 450 preferably extends beyond the first and second ends of the barbed suture 400. Although the present invention is not limited by any particular theory of operation, it is believed that winding a plurality of filaments around the elongated core 406 reinforces the barbed insert and provides a braided barbed insert having improved durability and/or strength. In one embodiment, the braid may be useful when the braided barbed suture is under tension. The barbs 448 of the first and second sets of barbs 408, 410 preferably project through the interstices of the braid 450.

In one embodiment, the barbed suture is made using a non-absorbable polymeric material, and a non-absorbable multi-filament polyester suture, commonly sold under the trademark ETHIBOND EXCEL polyester suture by Ethicon, Inc., with surgical needles attached to both ends of the suture. A pledget configured from biocompatible material such as a TEFLON® pledget, may be positioned in the middle of the polymeric anchoring section.

The barbed suture and the filaments wound around the suture for making the braid may be made of conventional, biocompatible, absorbable materials, non-absorbable materials, and combinations of absorbable and non-absorbable materials. Preferred non-absorbable materials suitable for both the barbed inserts and the filaments include polypropylene, a polymer blend of polyvinylidene fluoride and polyvinylidene fluoride-co-hexafluoropropylene, polyethylene, polyvinylidene fluoride (PVDF), polyesters, polyethylene terephthalate, glycol-modified polyethylene terephthalate, polytetrafluoroethylene, fluoropolymers, nylons etc. and the like, or copolymers of combinations thereof. Preferred absorbable polymeric materials suitable for both the barbed inserts and the filaments include polydioxanone, polyglactin, polyglycolic acid, copolymers of glycolide and lactide, polyoxaesters, and poliglecaprone. In certain preferred embodiments, these may include combinations of both absorbable and non-absorbable materials, especially for the filaments. In addition, metals or ceramics may be suitable for certain applications, such as instances where specific strength or corrosion resistance is necessary. In one preferred embodiment, the insert preferably includes a polymer blend of polyvinylidene fluoride and polyvinylidene fluoride-co-hexafluoropropylene material, and the braid preferably includes a polyethylene terephthalate material. In addition, any of these materials may have conventional surface modifications that include coatings, plasma treatments, therapeutics, and the like.

Figure 7B:
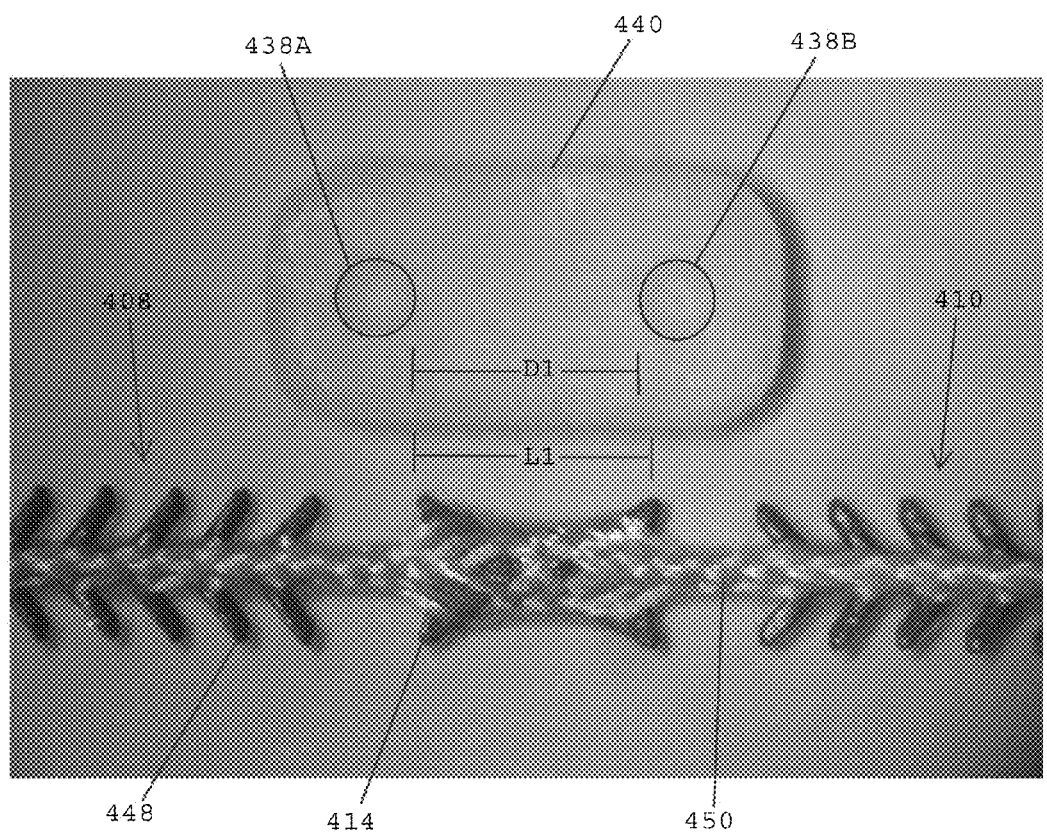
FIG. 7B shows a magnified view of the braided barbed suture and the pledget shown in FIG. 7A.

Referring to FIG. 7B, in one embodiment, the filaments are wound around the core and the stop 414. The barbs of the first and second sets of barbs 408, 410 desirably project between the interstices of the braid 450. In one embodiment, the braided barbed suture 400 is used in conjunction with a pledget 440, such as a pledget made of a biocompatible material such as a TEFLON® material, having a first opening 438A and a second opening 438B spaced from the first opening. In one embodiment, the distance $D_1$ between the spaced pledget openings 438A, 438B preferably matches the length $L_1$ of the stop 414. In one embodiment, the end walls of the stop may conform to the shape of the openings extending through the pledget.

Figure 8A:
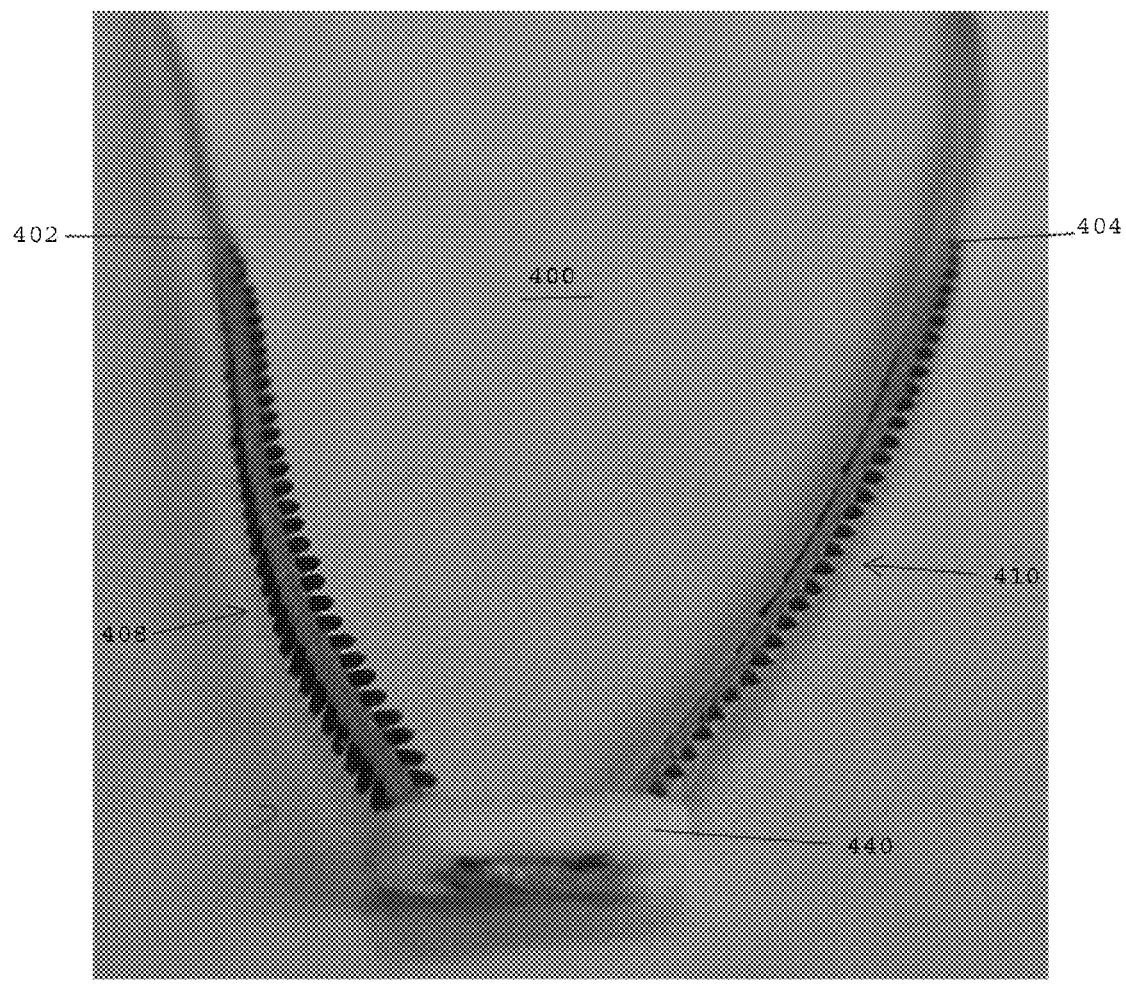
FIG. 8A shows a perspective view of the braided barbed suture and pledget of FIG. 7A assembled together.

Referring to FIG. 8A, in one embodiment, the first and second ends 402, 404 of the braided barbed suture 400 of FIG. 7A are passed through the first and second openings (not shown) of the pledget 440 so that the stop 414 within the central region 412 of the suture core is positioned between the first and second openings of the pledget 440. In one embodiment, a major face of the stop 414 preferably seats against an opposing major face of the pledget 440.

Figure 8B:
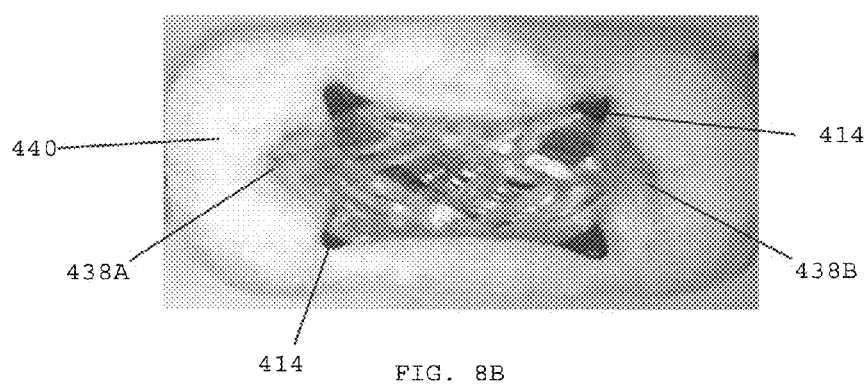
FIG. 8B shows a bottom view of the braided barbed suture and the pledget shown in FIG. 8A.

FIG. 8B shows the pledget stop 414 positioned between the first and second openings 438A, 438B of the pledget 440. The first and second legs of the braided barbed suture and the braid formed about the legs desirably extend through the first and second pledget openings 438A, 438B. In one embodiment, the plurality of filaments are preferably wound around the core of the suture and the pledget stop 414 for reinforcing the insert. In one embodiment, the filaments may reinforce and/or add strength to the braided barbed suture, particularly when the braided barbed suture is under tension.

Figure 9:
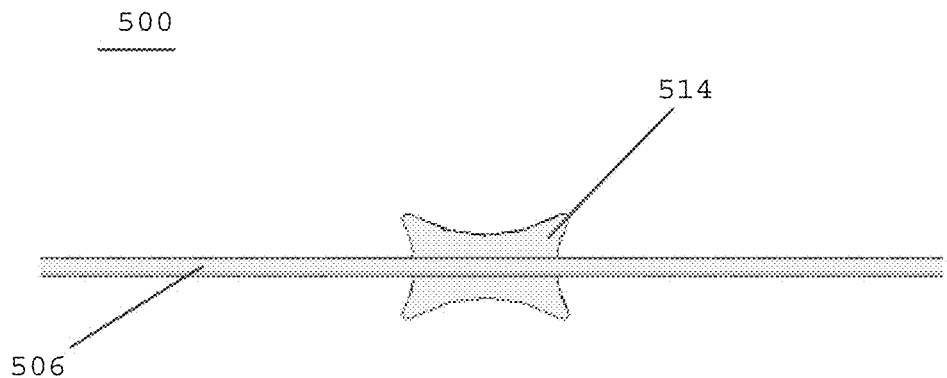
FIG. 9 shows a suture having a stopper in a central region thereof, in accordance with one embodiment of the present invention.

The full saddle, half saddle and tab shaped stops described above may also be provided on unbarbed sutures. Such sutures may be braided and/or unbraided. Referring to FIG. 9, in one embodiment, a suture 500 includes an elongated core 506 having a stop 514 that is similar to the two saddle stop shown in the embodiments of FIGS. 3A and 7A.

Figure 10:
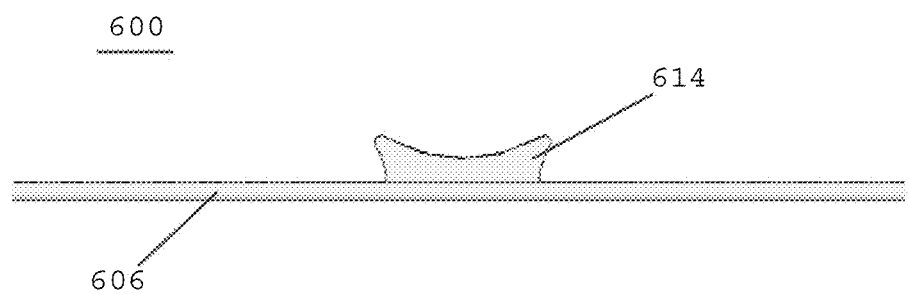
FIG. 10 shows a suture having a stopper in a central region thereof, in accordance with another embodiment of the present invention.

Referring to FIG. 10, in one embodiment, a suture 600 has an elongated core 606 and a single saddle stop 614 similar to that shown in the embodiment of FIG. 4.

Figure 11:
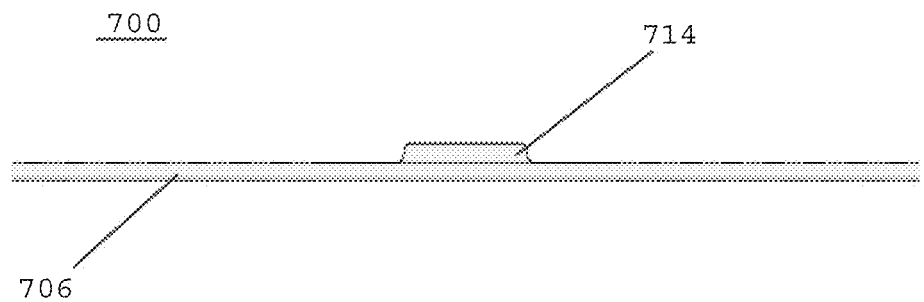
FIG. 11 shows a suture having a stopper in a central region thereof, in accordance with yet another embodiment of the present invention.

Referring to FIG. 11, in one embodiment, a suture 700 has an elongated core 706 and a tab-shaped stop 714 similar to that shown in the embodiment of FIG. 5. The stop 714 is preferably centrally located on the core 706 of the suture. In one embodiment, the stop preferably has a length that substantially matches the spacing between first and second openings on a pledget used herewith. In one embodiment, the sutures with stops shown in the embodiments of FIGS. 9-11 may be used without a pledget. In these embodiments, the stop may, by itself, function as a buttress for the suture.

Figure 12:
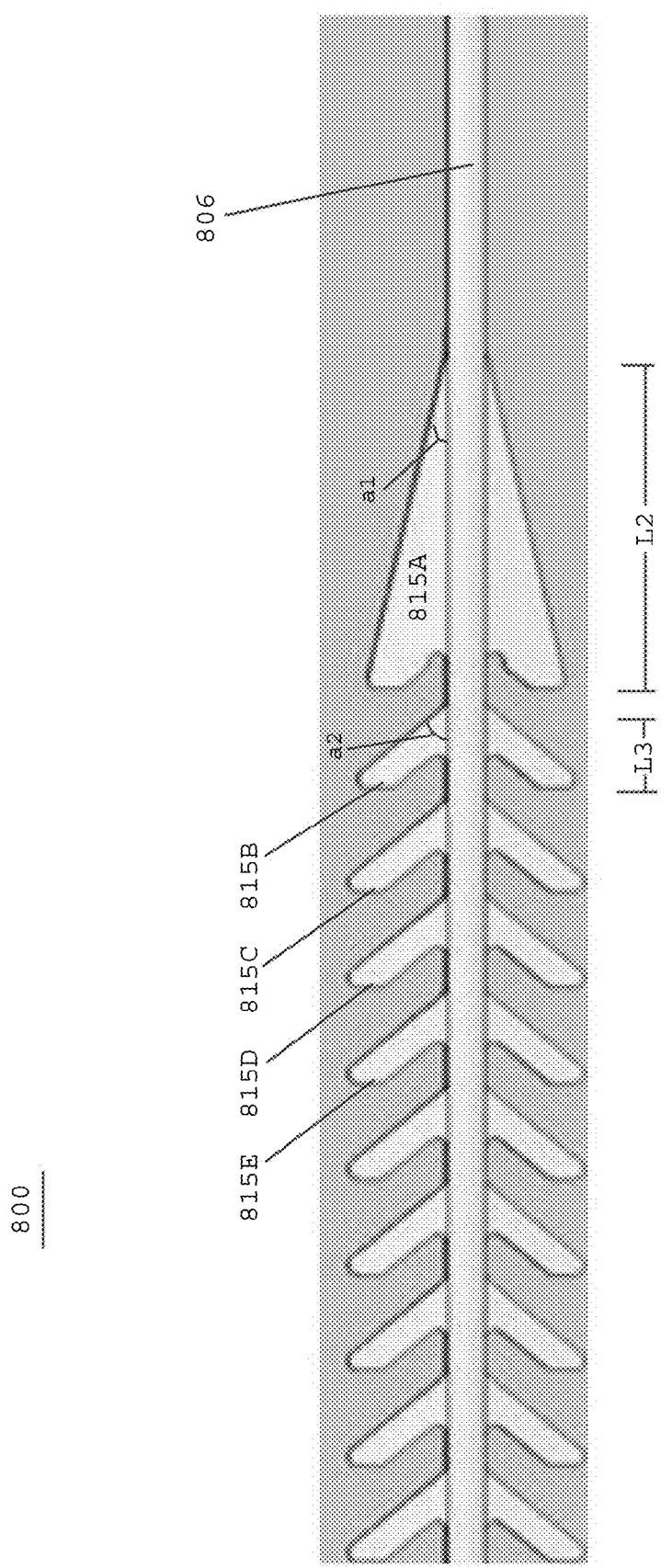
FIG. 12 shows a barbed suture having a leading arrow-shaped barb, in accordance with one embodiment of the present invention.

Referring to FIG. 12, in one embodiment, a barbed suture 800 includes an arrowhead shaped leading barb 815A that precedes a series of trailing barbs 815B-815E. The leading arrowhead shaped barb 815A has a length $L_2$ that is greater than the length $L_3$ of the trailing barbs 815B-815E. In one embodiment, the length $L_2$ of the leading barb 815A is about 0.1 inches and the lengths $L_3$ of the respective trailing barbs 815B-815E are about 0.03 inches. In one embodiment, the leading barb 815A has a length that is about 4× greater than the length of the trailing barbs 815B-815E. Because the length of the leading barb is greater than the length of the trailing barbs, the leading arrowhead shaped barb 815A tapers outwardly at an angle $a_1$ that is less than the angle $a_2$ of the trailing barbs 815B-815E. In one embodiment, a tangent line extending along the taper of the leading barb 815A extends to the outer edge of trailing barb 815B, which further extends to the outer edge of the trailing barb 815D. In one embodiment, the leading barb 815A tapers away from the core 806 at an angle of about 10-20° and the trailing barbs 815B-815E taper outwardly at an angle of about 50-60°. The more gradual outward taper of the arrowhead shaped leading barb 815A preferably allows for a smoother transition from the core 806 of the suture to the trailing 815B-815E as the suture is pulled through tissue or a sewing ring. Thus, the arrowhead-shaped leading barb 815A is preferably adapted to gradually distribute the pulling force required to pass the barbs through tissue or a sewing ring as opposed to a more abrupt angular transition from the core 806 to the trailing barbs 815B-815E, and as is found with the barbs of prior art barbed sutures. Although FIG. 12 shows an unbraided barbed suture, the arrowhead shaped leading barb of FIG. 12 may also be incorporated into a braided barbed suture.

In one embodiment, the barbs have a width (i.e. from one tip of the barb to the other tip of the same barb) that is great enough to extend beyond the braid when a barbed insert is combined with a braided structure so as to enable the barbs to engage tissue or to engage the fabric of an implant.

One or more features of any of the embodiments disclosed herein may be combined with one or more features of any of the other embodiments disclosed herein and still fall within the scope of the present invention. The present invention may also incorporate one or more of the embodiments disclosed in commonly assigned U.S. Patent Application Publication Nos. 2007/0005110 and 2007/0257395, and commonly assigned U.S. patent application Ser. Nos. 12/135,176; 12/140,311; 12/177,947; and 12/340,829, the disclosures of which are hereby incorporated by reference herein.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A surgical suture assembly comprising:
a surgical suture, the suture comprising
an elongated core including a first leg and a second leg;
a stop projecting from said elongated core between said first and second legs, said stop being integrally formed with and affixed to said elongated core to remain stationary relative to said elongated core, wherein said stop comprises a saddle projecting from a first side of said elongated core, said saddle having a first end, a second end, and a concave surface that extends along the length of said saddle between said first and second ends of said saddle, wherein said stop further comprises a second saddle projecting from a second side of said elongated core, said second saddle having a first end, a second end, and a second concave surface that extends along the length of said second saddle between said first and second ends of said second saddle; and
a pledget having first and second openings that are spaced from one another by a distance that matches the length of said stop, wherein said first leg of said elongated core extends through said first pledget opening, said second leg of said elongated core extends through said second pledget opening, and said stop extends between said first and second pledget openings, wherein a major face of said stop is seated against an opposing major face of said pledget.

2. The surgical suture assembly as claimed in claim 1, further comprising a plurality of filaments wound around said elongated core and said stop for forming a braid extending along said elongated core.

3. The surgical suture assembly as claimed in claim 1, wherein said stop defines the largest cross-sectional dimension of said core.

4. The surgical suture assembly as claimed in claim 1, wherein said first and second saddles of said stop are coplanar.

5. The surgical suture assembly as claimed in claim 1, further comprising:
a first set of barbs projecting from said first leg of said elongated core; and
a second set of barbs projecting from said second leg of said elongated core, wherein said stop projects from a central region of said elongated core located between said first and second sets of barbs.

6. The surgical suture assembly as claimed in claim 5, wherein said first set of barbs project in a first direction and said second set of barbs project in a second direction that is opposite the first direction.

7. The surgical suture assembly as claimed in claim 5, wherein said first and second sets of barbs are flexible, and wherein said stop is less flexible than said first and second sets of barbs.

8. A surgical suture assembly comprising:
a surgical suture, the suture comprising
an elongated core including a first leg, a second leg, and a central region located between said first and second legs;
a first set of barbs projecting from said first leg;
a second set of barbs projecting from said second leg;
a stop projecting from said central region of said elongated core, wherein said stop is integrally formed with and affixed to said elongated core to remain stationary relative to said elongated core; and
a pledget having first and second openings that are spaced from one another by a distance that matches the length of said stop, wherein said first leg extends through said first pledget opening, said second leg extends through said second pledget opening, and said stop extends between said first and second pledget openings, wherein a major face of said stop is seated against an opposing major face of said pledget.

9. The surgical suture assembly as claimed in claim 8, further comprising a braid formed around said elongated core and said stop.

10. The surgical suture assembly as claimed in claim 8, wherein said first and second sets of barbs are flexible, and wherein said stop is less flexible than said first and second sets of barbs.

11. The surgical suture assembly as claimed in claim 8, wherein said stop comprises at least one saddle projecting from said core, said at least one saddle having a first end, a second end, a concave surface that extends along the length of said at least one saddle between said first and second ends of said at least one saddle.

12. The surgical suture assembly as claimed in claim 8, wherein at least one of said first and second legs includes a lead barb having a more gradual outwardly projecting slope than a second barb that trails said lead barb.

13. The surgical suture assembly as claimed in claim 8, wherein said stop comprises a first end adjacent said first leg, a second end adjacent said second leg, and a surface between the first and second ends, the surface being one of concave or linear.

14. The surgical suture assembly as claimed in claim 8, wherein said stop comprises at least one saddle having at least one concave or linear surface.

15. The surgical suture assembly of claim 8, wherein said barbs are flexible.

16. A surgical suture assembly comprising:
a surgical suture, the suture comprising
an elongated core including a first leg and a second leg;
a first set of barbs projecting from said first leg;
a second set of barbs projecting from said second leg;
a stop projecting from said elongated core and being located between said first and second sets of barbs, wherein said stop is integrally formed with and affixed to said elongated core to remain stationary relative to said elongated core;
a braid surrounding said elongated core and said stop; and
a pledget having first and second openings that are spaced from one another by a distance that matches the length of said stop, wherein said first leg extends through said first pledget opening, said second leg extends through said second pledget opening, and said stop extends between said first and second pledget openings, wherein a major face of said stop is seated against an opposing major face of said pledget.

17. The surgical suture assembly as claimed in claim 16, wherein said braid comprises a plurality of filaments wound around said elongated core and said stop, and wherein barbs of said first and second sets of barbs extend through said braid.

18. The surgical suture assembly as claimed in claim 16, wherein said stop forms a concave or linear surface.

* * * * *